United States Patent [19]

Markusch et al.

[11] 4,355,138

[45] Oct. 19, 1982

[54] POLYISOCYANATE ADDUCTS WITH APOLAR SOLVENT COMPATIBILITY AND GOOD STORAGE STABILITY

[75] Inventors: Peter Markusch, McMurray, Pa.; George A. Hudson, deceased, late of Venetia, Pa.; by Richard L. White, administrator, Leverkusen, Fed. Rep. of Germany

[73] Assignee: Mobay Chemical Corporation, Pittsburgh, Pa.

[21] Appl. No.: 282,285

[22] Filed: Jul. 10, 1981

[51] Int. Cl.$^3$ .................... C08G 18/78; C07C 127/24
[52] U.S. Cl. .......................... 525/127; 260/453 AB; 260/453 SP; 528/59
[58] Field of Search .................. 260/453 SP, 453 AB; 528/59, 75, 80; 525/127

[56] References Cited

U.S. PATENT DOCUMENTS

| | | | |
|---|---|---|---|
| 3,124,605 | 3/1964 | Wagner | 260/453 |
| 3,201,372 | 8/1965 | Wagner | 260/77.5 |
| 3,358,010 | 12/1967 | Britain | 260/453 AB |
| 3,789,037 | 1/1974 | Miller | 260/16 |

OTHER PUBLICATIONS

Polyurethanes: Chemistry & Technology, vol. II Technology Saunders and Fritsch, 1964, pp. 468–477.

*Primary Examiner*—Dolph H. Torrence
*Attorney, Agent, or Firm*—Gene Harsh; Lawrence S. Pope; Thomas W. Roy

[57] ABSTRACT

The present invention is directed to light stable polyisocyanate adduct mixtures with an average functionality greater than 2.0 and an isocyanate content of between about 4 and 19 percent by weight based on solids, which has good compatibility with apolar solvents and good storage stability in a solution of polyisocyanate solvents. The polyisocyanate adduct mixtures are based on the reaction product of a polyisocyanate, preferably a biuret-containing polyisocyanate, with a first monohydroxy compound containing a saturated hydrocarbon chain of at least 8 carbon atoms and a second monohydroxy compound containing at least one polarity inducing group. Alternatively, both the saturated hydrocarbon chain and the polarity inducing group may be present in the same monohydroxy compound.

The present invention is additionally directed to the use of the polyisocyanate adduct mixtures in the process of curing alkyd or acrylic resins and to compositions containing the adduct mixture and alkyd or acrylic resins.

17 Claims, No Drawings

POLYISOCYANATE ADDUCTS WITH APOLAR SOLVENT COMPATIBILITY AND GOOD STORAGE STABILITY

FIELD OF THE INVENTION

This invention relates to polyisocyanate adduct mixtures which have good compatibility with apolar solvents and good storage stability in solution.

BACKGROUND OF THE INVENTION

It is well known that isocyanates may be added to isocyanate-reactive systems such as alkyd resins or acrylic resins to improve both the curing behavior and the properties of the cured coating. The preparation and use of urethane oils of this type are extensively discussed at pages 468 to 477 of *Polyurethanes: Chemistry and Technology*, Volume II Technology, Saunders and Frisch, Interscience 1964. It is also known that coatings prepared from aliphatic isocyanates impart superior light stability (resistance to yellowing, particularly on exposure to sunlight) as compared to aromatic isocyanates. A class of isocyanates which has been found to be particularly favorable for coating applications are aliphatic or cycloaliphatic polyisocyanates, especially the tris (isocyanato alkane) biurets such as those disclosed in U.S. Pat. Nos. 3,124,605 and 3,201,372. It has been found desirable to add such isocyanates to alkyd resin systems containing aliphatic solvents such as those used in the auto refinishing industry. Unfortunately, while these biuret-containing polyisocyanates, including the popular tris (isocyanato alkane) biurets, exhibit some degree of compatibility with the alkyd resins themselves, they display a high degree of incompatibility with the apolar solvents normally used in such systems. Since these solvents are both effective and economical in such systems, it was felt that the compatibility of the aliphatic polyisocyanates would have to be improved if they were to find practical utility in these systems.

In order to improve the compatibility of aliphatic biuret isocyanates with apolar solvents, it was proposed in concurrently filed application U.S. Ser. No. 282,206 filed July 10, 1981, to react these isocyanates with aliphatic or cycloaliphatic monohydroxy alcohols containing at least 8 carbon atoms. While these modified isocyanates exhibited increased compatibility with apolar solvents, they no longer formed storage stable solutions in the polar solvents normally used to lower the viscosity of isocyanates, since the isocyanate solvents are more polar than the apolar solvents used with the isocyanate-reactive systems.

It is therefore an object of the present invention to form polyisocyanate adducts which are compatible with apolar solvents and still maintain good storage stability in solution.

It is a further object of the present invention to provide polyisocyanate adducts which overcome the prior art problems associated with the use of isocyanates in isocyanate-reactive systems, such as alkyd resins or acrylic resins.

SUMMARY OF THE INVENTION

It has been discovered that light stable polyisocyanates with an average functionality greater than about 2.0 can be modified to be compatible with apolar solvents while still maintaining good storage stability in solution. These modifications are made by reacting a polyisocyanate, preferably a biuret-containing polyisocyanate, which has only aliphatically or cycloaliphatically bound isocyanate groups with (1) aliphatic or cycloaliphatic monohydroxy alcohols with at least 8 carbon atoms to improve apolar solvent compatibility, and (2) a monohydroxy compound which contains one or more polarity inducing groups comprising a member selected from the group consisting of ester groups, ether groups, aromatic rings or mixtures thereof in an amount sufficient to provide polyisocyanate adduct mixtures with good storage stability in polyisocyanate solvents.

In a preferred embodiment both the compatibility and solubility modifiers are combined into one adduct for reaction with the biuret-containing polyisocyanate.

The compatibility and solubility modifiers may each be used or the combined modifier may be used in an amount of between about 0.05 to 0.5 moles, preferably about 0.1 to 0.3 moles, and most preferably about 0.1 to 0.2 moles per equivalent of isocyanate. The reactants are selected to provide a final product with an average functionality greater than about 2.0, preferably greater than about 2.5, and to provide an isocyanate content of about 4 to 19 weight percent, preferably about 5 to 15 weight percent and most preferably about 8 to 13 weight percent based on solids.

DETAILED DESCRIPTION OF THE INVENTION

Suitable polyisocyanates to be used according to the present invention include trimerized aliphatic diisocyanates containing isocyanurate groups and adducts of trimethylol propane and aliphatic diisocyanates. The preferred aliphatic diisocyanate used to prepare polyisocyanate adducts is 1,6-hexamethylene diisocyanate. These polyisocyanates should have an average isocyanate functionality greater than about 2.0, preferably greater than about 2.5.

The preferred polyisocyanates to be used according to the present invention are light stable biuret-containing polyisocyanates with an average isocyanate functionality greater than about 2.0, preferably greater than 2.5. The light stability implies that the isocyanate groups will be either aliphatically or cycloaliphatically bound. The isocyanate free residue may be branched or linear and may carry substituents such as halogen, $NO_2$, an aryl group, an alkoxy group, an alkyl group or other groups which are inert to isocyanate groups. The polyisocyanate molecule should not carry any hydrogen atoms which are reactive with isocyanates such as hydroxyl or amine hydrogens.

The polyisocyanates may be prepared by methods well known to those skilled in the art and suitable methods of preparation are described in U.S. Pat. Nos. 3,124,605; 3,358,010; 3,903,127 and 4,051,165 all of which are incorporated herein by reference. The biuret polyisocyanates described in these patents and the biuret polyisocyanates prepared from the starting diisocyanates described in these patents are suitable for the present invention provided that their isocyanate groups are aliphatically or cycloaliphatically bound. Included among the suitable starting diisocyanates to prepare the biuret polyisocyanates are ethylene diisocyanate, trans-vinylidene diisocyanate, 1,3-bis(γ-isocyanatopropoxy)-2-methyl-2-propyl propane, tetramethylene diisocyanate, pentamethylene diisocyanate, hexamethylene diisocyanate, 1,3-cyclopentyl-diisocyanate, 4,4'-dicyclohexyl diisocyanate, 1,2-di(isocyanatomethyl)- cyclobutane, 1,3-bis-(isocyanatopropoxy)-2,2-dimethylpropane, 1,3-bis-(isocyanatopropyl)-2-methyl-2-propylpropane, 1-methyl-2,4-diisocyanatocyclohexane, 1-methyl-2,6-diisocyanatocyclohexane, bis-(4-isocyanatocyclohexyl)-methane, 1,4-diisocyanatocyclohexane and 1,3-diisocyanatocyclohexane, m- and p-xylylene diisocyanate, 1,3- and 1,4-bis(isocyanatomethyl)-cyclohexane, 3-isocyanatomethyl-3,5,5-trimethylcyclohexylisocyanate (isophorone diisocyanate or IPDI) and ethyl-2,6-diisocyanato-hexanoate.

Particularly preferred aliphatic, cycloaliphatic and araliphatic diisocyanates are hexamethylene diisocyanate, the isomeric mixture of 1-methyl-2,4-diisocyanatocyclohexane and 1-methyl-2,6-diisocyanatocyclohexane, bis-(4-isocyanatocyclohexyl)-methane, m- and p-xylylene diisocyanate, 1,3- and 1,4-bis-(isocyanatomethyl)-cyclohexane, isophorone diisocyanate, and methyl-substituted hexamethylene and pentamethylene diisocyanate.

The most preferred diisocyanates are unsubstituted alkyl diisocyanates, particularly those with 4 to 9 carbon atoms. Especially preferred of these is hexamethylene diisocyanate.

Particularly preferred biuret polyisocyanates are those of the formula:

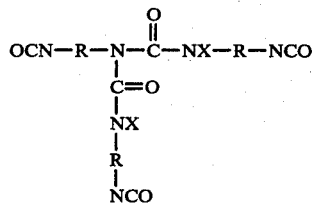

wherein R is an aliphatic or cycloaliphatic residue optionally substituted with alkyl or alkoxy groups, especially an alkyl or cycloalkyl residue and most preferably —(CH$_2$)$_6$—, and wherein X represents H or

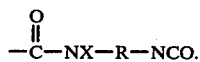

The compatibility modifier may be any saturated, straight or branched, aliphatic or cycloaliphatic monohydroxy compound which has 8 to 36 carbon atoms and an aliphatically or cycloaliphatically bound primary or secondary hydroxyl group. The alcohol should not have any groups as integral bonds or substituents which tend to impart polarity to its molecule such as ether, ester, urea, urethane or biuret bonds or aromatic rings. The alcohol preferably has between 12 and 30 carbon atoms and most preferably between 12 and 20 carbon atoms. It is preferred that the alcohol contain no groups which would increase the polarity of the alcohol molecule to any significant extent compared to a similar molecule without such a group. The polarity of the polyisocyanate-compatibility modifier adduct can be measured, among other methods, by determining the compatibility with apolar solvents such as straight-chained or branched alkyls. The most preferred alcohol residues are straight-chained. It is preferred that the alcohols be soluble in aliphatic or apolar solvents. Examples of suitable compatibility modifiers are hexadecanol, octadecanol, tetradecanol, dodecanol, 2,6,8-tri-methylnonan-4-ol, 2-t-butylcyclohexanol, 4-cyclohexyl-1-butanol, 3,3,5,5-tetramethylcyclohexanol and mixtures thereof.

The solubility modifier may be any monohydroxy alcohol which contains a polarity inducing group. Suitable polarity inducing groups are ether or ester bonds or aromatic rings, with ether or ester bonds being preferred. The solubility modifiers may be represented by the formula

A—OH wherein A is a saturated, straight or branched carbon chain which contains one or more polarity inducing groups. The hydroxy group is not required to be a terminal or primary hydroxy group and may be attached to any of the carbons of the carbon chain (A), or to any of the carbons of the aromatic ring(s). If more than one polarity inducing group is desired, it may be provided by incorporating repeating ether groups, ester groups or aromatic rings into the carbon chain (A), or by incorporating mixtures of these groups.

Examples of compounds containing more than one polarity inducing group which are suitable solubility modifiers are 2-(2-methoxyethoxy) ethanol, 2-(2-ethoxyethoxy) ethanol, 2-(2-butoxyethoxy) ethanol, 2-(2-hexoxyethoxy) ethanol and 2-(2-methoxy-methylethoxy)-1-methylethanol. In addition, homologues of these compounds containing more than one ether group as well as compounds containing more than one ester group are suitable.

In most instances, however, one ether or ester group is sufficient to provide an adequate solubility modifier, especially if the number of carbons between the hydroxy group and the polarity inducing group is kept to a minimum, preferably within 4 carbons.

Included among the compounds containing one ester or ether group are those represented by the formula:

Y$_1$—R$_1$—Q—R$_2$—Y$_2$ wherein Q is —O—,

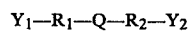

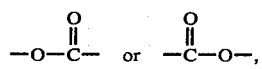

R$_1$ and R$_2$ may be the same or different and represent saturated, straight or branched, carbon chains of 1 to 7 carbon atoms; and either Y$_1$ or Y$_2$ is —OH with the other being hydrogen. The hydroxy substituent may be attached to any of the carbons of the R$_1$ or R$_2$ chains. R$_1$ and R$_2$ preferably contain 1 to 4 carbons. As the number of carbons increase between the hydroxy group and the polar inducing group, the polarity is reduced, thus decreasing the effect of the solubility modifier. On the nonhydroxy side as R increases in length, the weight of the adduct formed by the reaction with the polyisocyanate increases, and thereby reduces the weight percent of isocyanate groups in the final product.

Examples of suitable solubility modifiers embraced by this formula are: 2-methoxyethanol, 2-ethoxyethanol, 2-butoxyethanol, 2-hexoxyethanol, 2-methoxy-1-methylethanol, 2-propoxy-1-methylethanol, 2-butoxy-1-methylethanol, 2-hydroxyethylacetate, ethyl lactate and butyl lactate.

Other suitable solubility modifiers are aromatic compounds or substituted aromatic compounds. If the aromatic ring is monosubstituted, the substituent is preferably a saturated, straight or branched chain of up to 7 carbon atoms, preferably 1 to 4 carbons. The hydroxy group may be attached to this substituent, preferably within 4 carbons of the aromatic ring or it may be attached directly to the aromatic ring. Examples of aromatic solubility modifiers are phenol, benzyl alcohol, 5-phenyl-1-pentanol, 1-phenyl-1-propanol or o-, m- and p- methyl phenethyl alcohol.

If multiple polarity inducing groups are desired, then the above substituent may also contain ether or ester bonds or additional aromatic rings. The ether and ester groups are preferred due to the increased weight of the additional aromatic rings. Alternatively, the multiple polarity inducing groups may be attached to the aromatic ring through additional substituents. When more than one polarity inducing group is present, regardless of the number of substituents, the hydroxy group may be attached to the carbons of any of the substituents or it may be attached directly to the aromatic ring.

In a preferred embodiment of the present invention, the solubility and compatibility modifiers are combined into one adduct for subsequent reaction with the polyisocyanates. The basic requirement for a combined modifier is that it contains (a) the saturated, straight or branched carbon chain characteristic of the compatibility modifier;

(b) one or more polarity inducing groups; and (c) one hydroxyl group.

Any compound containing these components is suitable for use as a combined modifier provided that it satisfies the criteria previously outlined for the individual compatibility and solubility modifiers. For example, multiple polarity inducing groups may be incorporated; however, if the combined modifiers only contain one polarity inducing group, the hydroxyl group should be attached within 4 carbons of the polarity inducing group.

The formula $Y_1—R_1—Q—R_2—Y_2$ has previously been given as an example of a solubility modifier. In order to convert this modifier into a combined modifier, $R_1$ or $R_2$ should be a saturated, straight or branched chain of 8 to 36 carbons, preferably 12 to 20 carbons, and most preferably 12 to 16 carbons. The remaining $R_1$ or $R_2$ is as defined above. It is again noted that as the number of carbon atoms increases between the hydroxy group and the polar inducing group, the effect of the solubility component decreases. Examples of combined modifiers are 2,2,4-trimethylpentanediol-1,3-monoisobutyrate, n-dodecyl-2-hydroxy-n-propylether and n-hexadecyl-2-hydroxy-n-propylether.

The other previously described solubility modifiers may also be converted into combined modifiers by increasing the length of any short carbon chains contained in the modifier into a chain which contains 8 to 36 carbon atoms, preferably 12 to 20 carbon atoms and most preferably 12–16 carbon atoms. Additionally, to convert solubility modifiers containing aromatic rings into combined modifiers an additional carbon chain of the above-mentioned length may be attached to the aromatic ring. For example, if a $C_{12}$–$C_{16}$ carbon chain is attached to benzyl alcohol (a solubility modifier) the newly formed compound, dodecyl benzyl alcohol, would be a combined modifier. Another example of this type of modifier is dodecyl phenol.

The previously discussed conversions of solubility modifiers into combined modifiers are also applicable to solubility modifiers containing multiple polarity inducing groups.

The use of a combined solubility-compatibility modifier is advantageous when a high weight percent content of isocyanate groups in the final product is desired since only one isocyanate group is needed to incorporate the modifier. When separate compatibility and solubility modifiers are used, two isocyanate groups are required to incorporate the modifiers, thus reducing the isocyanate content of the final product. Another advantage of using combined modifiers when high isocyanate contents are desired is that their total weight will be less than that of comparable separate modifiers.

The polyisocyanate and the monohydroxy-containing solubility, compatibility or solubility-compatibility modifiers may be reacted under any thermal and catalytic conditions which give rise to the formation of urethane and/or allophanate bonds, preferably urethane bonds. The temperature should be sufficiently high to effect reaction within commercially acceptable times, but low enough to avoid significant degradation of the polyisocyanate or the modifiers such as by destruction of the biuret bonds when biuret-containing polyisocyanates are used. Suitable reaction conditions including temperatures and catalysts are well known to those skilled in the art and a useful compilation is contained in *Polyurethanes: Chemistry and Technology*, Volume I, Chemistry, Saunders and Frisch, Interscience, 1962.

The modified polyisocyanate adduct may be formed in the presence of any of the catalysts known to promote hydroxyl-isocyanate reactions. A number of suitable catalysts are discussed at pages 161 to 173 of *Polyurethanes: Chemistry and Technology*, Volume I. Some suitable catalysts and other reaction conditions for reacting hydroxyl-bearing compounds and biuret-containing polyisocyanates are discussed in U.S. Pat. No. 3,201,372, incorporated herein by reference.

The most preferred embodiment is to conduct the polyisocyanate addition reaction at ambient temperatures or above in the absence of any catalysts, e.g. room temperature to about 70° C. The absence of catalysts avoids the necessity of subsequently inactivating the catalyst.

The modified polyisocyanate adduct may be formed in substance or in the presence of suitable solvents. Suitable solvents should be inert to isocyanate groups, i.e., they should not contain any hydrogen groups readily reactive with NCO groups.

The adduct mixture may also be prepared by reacting the monohydroxy-containing modifier with the diisocyanate used to form the polyisocyanate either before or during the formation of the polyisocyanate. However, it is preferred to form the adduct after formation of the polyisocyanate.

The order of addition for the reactants is not critical. For example, the solubility modifier can be added to the polyisocyanate followed by the addition of the compatibility modifier, or vice-versa. In another embodiment, the polyisocyanate could be added to either of the modifiers followed by addition of the remaining modifier or both modifiers could be added initially before the polyisocyanate addition. In a further embodiment each of the modifiers could be reacted with the separate polyisocyanate solutions and the resulting adducts could be mixed to form the final product. This embodiment is less preferred since the final product mixture has reduced compatibility with apolar solvents when compared to adducts formed from a single solution of polyisocyanates.

The relative compatibility of the adduct mixtures of the present invention with apolar solvents is determined by dissolving the adduct mixture in a conventional isocyanate solvent and subsequently titrating an apolar solvent into the solution until some precipitation occurs, normally indicated by cloudiness. For determining the relative compatibility between different polyisocyanate adduct mixtures, the isocyanate solvent may be any solvent in which the polyisocyanate adduct mixture has a reasonable degree of solubility. Among the more common suitable solvents are cellosolve acetate, xylene, methylethylketone, and the like. Of particular interest are those solvent systems which have less than 20 percent by volume of photochemically reactive solvents and particularly those which meet the standards of Rule 66 of California's air pollution code. The particular solvent system in which the compatibility test is performed is felt to have some effect on the results but not on the relative rankings of polyisocyanates tested, i.e., a more compatible polyisocyanate will remain so regardless of the solvent system, although its absolute compatibility may change. The titrant may be any apolar solvent miscible with the solvent system. Of particular interest are those apolar solvents typically used with alkyd resins such as aliphatic solvents. Among these are naphtha, hexane, heptane and mineral spirits.

In order to determine the storage stability of the polyisocyanate adducts mixtures when in solution in common polyisocyanate solvents, samples are subjected to the Cold Cycle Test (CCT). To conduct this test, the samples are cooled to −20° C. for a period of twelve hours and then allowed to warm to room temperature. This test is repeated three times. As the samples warm to room temperature following the third cold cycle, they should become clear. If they remain cloudy, they have not passed the Cold Cycle Test. Any cloudiness can be removed by heating to 60° C. to 70° C. for a short period of time; however, samples which require this additional heating to become clear, have not passed the test. Good storage stability may be achieved when polyisocyanate adduct mixtures dissolved in xylene at a 40 weight percent solids content are capable of passing the Cold Cycle Test.

In the examples which follow, adducts were prepared from DES N 100 (a commercially available biuret of hexamethylene diisocyanate prepared in accordance with U.S. Pat. No. 3,903,127) and various monohydroxy compounds. The biuret was first mixed with a portion of the solvent and then the monohydroxy compound, dissolved in additional solvent was added dropwise with stirring at room temperature. After the addition of the monohydroxy compound was complete and while maintaining stirring, the mixture was heated to between 60° and 70° C. for three hours. After completion of the reaction, the mixture was cooled to room temperature. Additional solvent was then added, if necessary, until a 40 weight percent solids content was obtained. The previously discussed Cold Cycle Test was then conducted.

The compatibility of the adduct mixture with apolar solvents was then determined by titrating heptane into solutions of the polyisocyanate adduct mixtures in polyisocyanate solvents (the Heptane Tolerance Test). Heptane was chosen as the titrant because it is readily available in reagent purity and it is believed to be fairly representative of apolar solvents. All tests were conducted with the polyisocyanate adduct mixtures at a 40 weight percent solids content using 50 g. specimens. Good compatibility of these adduct mixtures with apolar solvents may be obtained when the amount of heptane titrated, before a 40 weight percent solution of the adduct mixture in xylene turns cloudy, is greater than or equal to 6 ml.; however, amounts greater than about 9 ml are preferred with amounts greater than about 15 ml being most preferred. Subsequent testing with commercially available alkyd systems (resin and solvents) verified the compatibility results of the heptane titrations.

The following Table sets forth the monohydroxy modifier, the number of equivalents of the modifier based on 1 equivalent weight of the biuret (approximately 195 g), the solvent used, whether the mixture passed the Cold Cycle Test (CCT) and the amount of heptane titrated in milliliters before the mixture turned cloudy in accordance with the Heptane Tolerance Test (HTT).

| EXAMPLE | MODIFIER | EQUIVALENTS | SOLVENT | CCT | HTT(ml) |
|---|---|---|---|---|---|
| 1 | n-hexadecanol[1] | 0.1 | A | Pass | 19.0 |
|   | 2-hexoxyethanol[2] | 0.1 |   |   |   |
| 2 | n-hexadecanol | 0.2 | B | Pass | 15.6 |
|   | 2-hexoxyethanol | 0.08 |   |   |   |
| 3 | n-hexadecanol | 0.2 | B | Pass | 15.7 |
|   | 2-hexoxyethanol | 0.1 |   |   |   |
| 4 | n-hexadecanol | 0.2 | B | Pass | 14.5 |
|   | 2-hexoxyethanol | 0.1 |   |   |   |
| 5 | n-hexadecanol | 0.2 | B | Pass | 14.3 |
|   | 2-hexoxyethanol | 0.12 |   |   |   |
| 6 | n-hexadecanol | 0.1 | A | Pass | 13.5 |
|   | benzyl alcohol[2] | 0.1 |   |   |   |
| 7 | n-hexadecanol | 0.2 | B | Pass | 12.4 |
|   | benzyl alcohol | 0.08 |   |   |   |
| 8 | n-hexadecanol | 0.2 | B | Pass | 10.0 |
|   | benzyl alcohol | 0.1 |   |   |   |
| 9 | n-hexadecanol | 0.2 | B | Pass | 10.0 |
|   | benzyl alcohol |   |   |   |   |
| 10 | nonylphenol[3] | 0.1 | B | Pass | 4.6 |
| 11 | nonylphenol | 0.2 | B | Pass | 5.4 |
| 12 | nonylphenol | 0.3 | B | Pass | 6.2 |
| 13 | nonylphenol | 0.4 | B | Pass | 8.2 |
| 14 | nonylphenyl | 0.5 | B | Pass | 11.6 |
| 15 | Texanol[3,4] ester-alcohol | 0.05 | C | Pass | 10.0 |
| 16 | Texanol ester-alcohol | 0.1 | C | Pass | 10.0 |
| 17 | Texanol ester-alcohol | 0.15 | C | Pass | 11.0 |

-continued

|    | MODIFIER | EQUIVALENTS | SOLVENT | CCT | HTT(ml) |
|---|---|---|---|---|---|
| 18 | Texanol ester-alcohol | 0.2 | C | Pass | 10.0 |
| 19 | Texanol ester-alcohol | 0.25 | C | Pass | 11.0 |
| 20 | Texanol ester-alcohol | 0.3 | C | Pass | 14.5 |
| 21 | n-dodecyl-2-hydroxy-n-propylether[3] | 0.3 | B | Pass | 20.0 |
| 22 | n-dodecyl-2-hydroxy-n-propylether | 0.5 | B | Pass | 40+ |
| 23 | n-hexadecyl-2-hydroxy-n-propylether[3] | 0.2 | B | Pass | 14.0 |
| 24 | n-hexadecanol Texanol ester-alcohol | 0.1 0.1 | C | Pass | 17.6 |
| 25 | n-hexadecanol Texanol ester-alcohol | 0.2 0.1 | B | Pass | 14.1 |
| 26 | n-hexadecanol Texanol ester-alcohol | 0.2 0.12 | B | Pass | 14.8 |
| COMPARISON EXAMPLES | | | | | |
| 27 | n-decanol[1] | .1 | A | Fail | 6.4 |
| 28 | cyclohexanol | .1 | A | — | 4.8 |
| 29 | Esterdiol[5] tetradecanol[1] | .05 .05 | B | — | 3.7 |
| 30 | tripropolyeneglycol tetradecanol | .05 .05 | B | — | 3.4 |
| 31 | tetradecanol | .2 | B | Fail | 6.2 |
| 32 | n-hexadecanol | .2 | B | Fail | 14.4 |
| 33 | butanol | .3 | D | — | 3.4 |
| 34 | benzyl alcohol | .1 | B | Pass | 2.4 |
| 35 | benzyl alcohol | .2 | B | Pass | 2.4 |
| 36 | benzyl alcohol | .3 | B | Pass | 1.4 |
| 37 | ε-caprolactam | .1 | B | Pass | 3.4 |
| 38 | ε-caprolactam | .2 | B | Pass | 4.0 |
| 39 | ε-caprolactam | .3 | B | Pass | 4.0 |
| 40 | ε-caprolactam | .4 | B | Pass | 4.4 |
| 41 | ε-caprolactam | .5 | B | Pass | 4.2 |
| 42 | 1-hexadecylamine | .2 | B | Fail | — |
| 43 | 2-hydroxyethylacetate[2] | .2 | B | Pass | 2.4 |
| 44 | ethylacetoacetate | .2 | B | Pass | 4.4 |
| 45 | ethylacetoacetate | .4 | B | Pass | 5.2 |

[1] = compatibility modifier
[2] = solubility modifier
[3] = combined modifier
[4] = a trademark of Kodak, 2,2,4-trimethylpentanediol-1,3-monoisobutyrate
[5] = a trademark of Union Carbide, 2,2-dimethyl-3-hydroxypropyl-2,2-dimethyl-3-hydroxypropionate.
A = toluene
B = xylene
C = 8% xylene, 12% toluene, 30% butyl acetate and 50% methylethylketone
D = isobutylisobutyrate.

Examples 1-9 demonstrate the use of separate compatibility and solubility modifiers for producing polyisocyanate adduct mixtures which exhibit compatibility with apolar solvents, as shown by the Heptane Tolerance Test, and good storage stability, as shown by the Cold Cycle Test.

Examples 10-23 demonstrate the use of combined modifiers. These modifiers also produce polyisocyanate adduct mixtures which exhibit compatibility with apolar solvents as well as good storage stability. When using nonylphenol higher amounts are required to produce acceptable heptane tolerance values. This is believed to be due to the fact that the hydrocarbon chain (nonyl) does not contain the preferred numbers of carbon atoms (greater than 12) and consequently, additional amounts of this modifier are required.

Examples 24-26 show that combined modifiers may be mixed with additional quantities of compatibility modifiers. This combination of modifiers is used when high heptane tolerance values are desired. Alternatively, combined modifiers may be used with solubility modifiers when greater storage stability is required. The same results could also be obtained by simply using increased amounts of combined modifiers since this will increase both compatibility and storage stability. The disadvantage of using excess amounts of modifiers is that they reduce the isocyanate content of the polyisocyanate adduct mixture.

The comparison examples demonstrate the criticality of using modifiers which provide compatibility and storage stability. When only using compatibility modifiers (Examples 27, 31 and 32), the adducts do not pass the Cold Cycle Test. By only using solubility modifiers (Examples 34-36 and 43) the heptane tolerance values are deficient.

Examples 28 and 33 indicate that unless the length of the hydrocarbon chain is sufficient, the optimum heptane tolerance values are not achieved. The use of polyhydroxy compounds (Examples 29 and 30) also results in polyisocyanate adduct mixtures which do not pass the Heptane Tolerance Test.

Insufficient results are also obtained when using amines (Example 42) in place of monohydroxy compounds and when using known blocking agents for isocyanate groups (Examples 37-41, 44 and 45).

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A light stable polyisocyanate adduct mixture with an average functionality greater than about 2.0 and an isocyanate content of between about 4 and 19 percent by weight based on solids, which has good compatibility with apolar solvents and good storage stability in a solution of polyisocyanate solvents comprising the reaction product of
   (a) a polyisocyanate with an average functionality greater than about 2.0 and containing only aliphatically or cycloaliphatically bound isocyanate groups with
   (b) about 0.05 to 0.5 moles per equivalent of isocyanate groups of a saturated, straight or branched, aliphatic or cycloaliphatic monohydric alcohol which contains at least 8 carbon atoms and
   (c) about 0.05 to 0.5 moles per equivalent of isocyanate groups of a monohydroxy compound which contains one or more polarity inducing groups comprising a member selected from the group consisting of ester groups, ether groups aromatic rings or mixtures thereof,
   and/or the reaction product of (a) and
   (d) about 0.05 to 0.5 moles per equivalent of isocyanate groups of a monohydroxy compound which contains
      (1) a saturated, straight or branched hydrocarbon chain having at least about 8 carbon atoms, and
      (2) one or more polarity inducing groups comprising a member selected from the group consisting of ester groups, ether groups, aromatic rings or mixtures thereof.

2. The polyisocyanate adduct mixture of claim 1 wherein components (b) and (c) are each present in an amount between about 0.1 to 0.3 moles per equivalent of isocyanate groups.

3. The polyisocyanate adduct mixture of claim 1 wherein component (d) is present in an amount between about 0.1 to 0.3 moles per equivalent of isocyanate groups.

4. The polyisocyanate adduct mixture of claim 2 or 3 wherein the isocyanate content of the adduct mixture is about 5 to 15 weight percent based on solids.

5. The polyisocyanate adduct mixture of claim 1 wherein component (a) is a biuret-containing polyisocyanate.

6. A light stable polyisocyanate adduct mixture with an average functionality greater than about 2.0 and an isocyanate content of between about 4 and 19 percent by weight based on solids, which has good compatibility with apolar solvents and good storage stability in a solution of polyisocyanate solvents comprising the reaction product of
   (a) a biuret-containing polyisocyanate with an average functionality greater than about 2.0 and containing only aliphatically or cycloaliphatically bound isocyanate groups with
   (b) a saturated, straight or branched, aliphatic or cycloaliphatic monohydric alcohol which contains at least 8 carbon atoms in an amount sufficient to provide good compatibility of said polyisocyanate adduct mixture with apolar solvents and
   (c) a monohydroxy compound which contains one or more polarity inducing groups comprising a member selected from the group consisting of ester groups, ether groups, aromatic rings or mixtures thereof, in an amount sufficient to provide said polyisocyanate adduct mixture with good storage stability in polyisocyanate solvents,
   and/or the reaction product of (a) and
   (d) a monohydroxy compound which contains,
      (1) a saturated, straight or branched hydrocarbon chain having at least about 8 carbon atoms, and
      (2) one or more polarity inducing groups comprising a member selected from the group consisting of ester groups, ether groups aromatic rings or mixtures thereof,
   in an amount sufficient to provide said polyisocyanate adduct mixture with good compatibility with apolar solvents and good storage stability in polyisocyanate solvents.

7. The polyisocyanate adduct mixture of claim 1 or 6 wherein component (a) is represented by the formula:

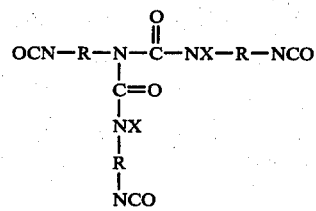

wherein
R is an aliphatic or cycloaliphatic residue, optionally containing alkyl or alkoxy substituents, and
X represents H or

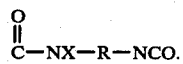

8. The polyisocyanate adduct mixture of claim 6 wherein component (a) is represented by the formula:

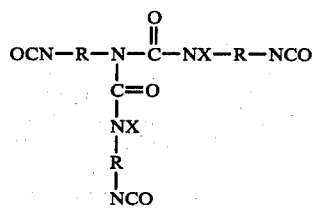

wherein
R represents —(CH$_2$)$_6$—, and
X represents H or

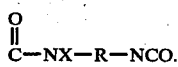

9. The polyisocyanate adduct mixture of claim 2, 6 or 8 wherein component (b) contains 12 to 20 carbon atoms.

10. The polyisocyanate adduct mixture of claim 1, 6 or 8 wherein component (c) is represented by the formula:

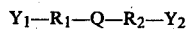

wherein
Q is —O—,

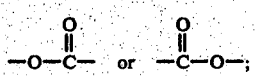

$R_1$ and $R_2$ may be the same or different and represent saturated, straight or branched hydrocarbon chains of 1 to 7 carbon atoms; and either $Y_1$ or $Y_2$ is —OH with the other being hydrogen.

11. The polyisocyanate adduct mixture of claim 10 wherein $R_1$ and $R_2$ contain 1 to 4 carbon atoms.

12. The polyisocyanate adduct mixture of claim 1, 6 or 8 wherein component (c) is benzyl alcohol, 2-hexoxyethanol or 2-hydroxyethylacetate.

13. The polyisocyanate adduct mixture of claim 1, 6 or 8 wherein component (d) is represented by the formula:

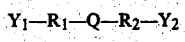

wherein
Q is —O—,

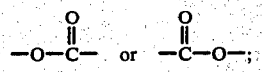

$R_1$ or $R_2$ represents a saturated, straight or branched, hydrocarbon chain of 8 to 36 carbon atoms while the remaining $R_1$ or $R_2$ represents a saturated, straight or branched hydrocarbon chain of 1 to 7 carbon atoms;
and
either $Y_1$ or $Y_2$ is —OH with the other being hydrogen.

14. The polyisocyanate adduct mixture of claim 13 wherein $R_1$ or $R_2$ represents a hydrocarbon chain of 12 to 20 carbon atoms while the remaining $R_1$ or $R_2$ represents a hydrocarbon chain of 1 to 7 carbon atoms.

15. The polyisocyanate adduct mixture of claim 1, 6 or 8 wherein component (d) is 2,2,4-trimethylpentanediol-1,3 monoisobutyrate, n-dodecyl-2-hydroxy-n-propyl-ether or n-hexadecyl-2-hydroxy-n-propylether.

16. In the process of curing apolar solvent-containing solutions of alkyd resins or acrylic resins with polyisocyanates, the improvement comprising using the polyisocyanate adduct mixture of claim 1, 6 or 8 as the polyisocyanate.

17. The composition comprising
(a) apolar solvent-containing solutions additionally containing a member selected from the group consisting of alkyd resins and acrylic resins, and
(b) the polyisocyanate adduct mixture of claim 1, 6 or 8.

* * * * *